United States Patent [19]

Goegelman et al.

[11] Patent Number: 5,290,804
[45] Date of Patent: Mar. 1, 1994

[54] ANTHELMINTIC MILBEMYCIN ANALOGS OF NOVEL MICROORGANISMS

[75] Inventors: Robert T. Goegelman, Linden, N.J.; Elvira Munguira; Maria T. Diez Matas, both of Madrid, Spain; Ruth S. Sykes; Yu L. Kong, both of Edison, N.J.; Jerrold M. Liesch, Princeton Junction, N.J.; Gregory L. Helms, Fanwood, N.J.; E. Tracy Turner Jones, Edison, N.J.

[73] Assignee: Merck & Co., Inc., Rahway, N.J.

[21] Appl. No.: 867,573

[22] Filed: Apr. 13, 1992

Related U.S. Application Data

[63] Continuation-in-part of Ser. No. 694,165, May 1, 1991, abandoned.

[51] Int. Cl.$^5$ .................. A61K 31/365; C07D 315/00
[52] U.S. Cl. ..................................... 514/450; 549/264
[58] Field of Search ......................... 514/450; 549/264

[56] References Cited

U.S. PATENT DOCUMENTS 3,950,360  9/1973  Aoki et al. .................. 260/343.2
4,778,809  10/1988  Maienfisch et al. ............. 514/450

FOREIGN PATENT DOCUMENTS 0186043  7/1986  European Pat. Off. .
0253767  7/1986  European Pat. Off. .
0298423  7/1987  European Pat. Off. .
0303933  8/1987  European Pat. Off. .
0246739  11/1987  European Pat. Off. .
2187778  1/1974  France .
0016894  1/1984  Japan .
214553  6/1989  New Zealand .
2168345  6/1980  United Kingdom .
2176182  12/1986  United Kingdom .

OTHER PUBLICATIONS

Shirling et al., International J. Systematic Bacteriology, 16, pp. 313-340, Jan. 1986.
Kurtzman et al., International J. Systematic Bacteriology, 30, pp. 208-216, Jan. 1980.

Primary Examiner—C. Warren Ivy
Assistant Examiner—A. A. Owens
Attorney, Agent, or Firm—Sylvia A. Ayler; Mark R. Daniel; Joseph F. DiPrima

[57] ABSTRACT

There is disclosed a series of macrolides isolated from the fermentation broth of microorganisms identified as MA-6825, MA-6864 and MA-6865. The structure of the novel compounds isolated from the microorganisms is presented based upon analytical studies. The compounds are highly potent antiparasitic, insecticidal, and anthelmintic agents and are related to the class of macrolides known as milbemycins. Compositions for such uses are also disclosed.

5 Claims, No Drawings

ANTHELMINTIC MILBEMYCIN ANALOGS OF NOVEL MICROORGANISMS

CROSS REFERENCE TO RELATED APPLICATIONS

This application is a continuation-in-part of our co-pending application Ser. No. 694,165, filed May 1, 1991 now abandoned.

BACKGROUND OF THE INVENTION

The instant novel compounds are related to the milbemycin compounds disclosed in U.S. Pat. No. 3,950,360. However the instant compounds possess significant structural differences which readily differentiate them from the prior art compounds.

SUMMARY OF THE INVENTION

This invention is concerned with novel chemical compounds. In particular, it is concerned with novel macrocyclic lactones which are produced by the fermentation of a nutrient medium with a strain of the microorganism *Streptomyces hygroscopicus*MA-6825, MA-6864 or MA-6865.

Thus, it is an object of this invention to provide for such novel compounds, and a method for preparing such products microbiologically. It is a further object of this invention to provide for the recovery and purification of such compounds from the fermentation broth. These substances have anti-parasitic and insecticidal activity, in particular anthelmintic, acaracidal and nematocidal activity, and it is, thus, an additional object of this invention to provide novel antiparasitic and insecticidal compositions containing the disclosed compounds. Further objects of this invention will become apparent from the following description of this invention.

DESCRIPTION OF THE INVENTION

In accordance with this invention, novel substances are described, which are prepared by growing under controlled conditions, a previously undescribed strain of microorganism, *Streptomyces hygroscopicus*MA-6825, MA-6864 or MA-6865. The compounds are obtained by fermentation and recovered in substantially pure form as described herein.

Based on taxonomic studies, the microorganism capable of producing these compounds is of a new strain of the microorganism *Streptomyces hygroscopicus*. The cultures are designated MA-6825, MA-6864 and MA-6865 in the culture collection of Merck & Co., Inc., Rahway, N.J. A sample of these cultures, capable of producing the herein described compounds, have been deposited on Jan. 28, 1991 under the Budapest Treaty on the International Recognition of the Deposit of Microorganisms for the Purposes of Patent Procedure in the permanent culture collection of the American Type Culture Collection at 12301 Parklawn Drive, Rockville, Md. 20852, and have been assigned the accession numbers ATCC 55144 for MA-6825, ATCC 55145 for MA-6864 and ATCC 55146 for MA-6865.

The morphological and cultural characteristics of *Streptomyces hygroscopicus* MA-6825 are set forth below:

We have compared culture MA-6825 with Sankyo's milbemycin patent strain *Streptomyces hygroscopicus* subsp *aureolacrimosis*, MA-4830. The following is a general description of these strains. Observations of growth, general cultural characteristics and carbon source utilization were made in accordance with the methods of Shirling and Gottleib (*Internat. J. System. Bacteriol.* 16: 313–340). Chemical composition of the cells was determined using the methods of Lechevalier and Lechevalier (in *Actinomycete Taxonomy*, A. Dietz and D. W. Thayer, Ed. Society for Industrial Microbiology, 1980). Coloration of the culture was determined by comparison with color standards contained in the Inter-Society Color Council-National Bureau of Standards Centroid Color Charts (U.S. Dept. of Commerce National Bureau of Standards supplement to NBS Circular 553, 1985). DNA-DNA homology of the strains was determined by the method described by Kurtzman, et al. (Int. J. Syst. Bacteriol. 30: 208–216).

Analysis of Cell Wall Composition—MA-4830

Peptidoglycan contains L-diaminopimelic acid. Whole cell carbohydrate analysis reveals glucose and traces of xylose. MA-6825—Peptidoglycan contains L-diaminopimelic acid. Whole cell carbohydrate analysis reveals glucose and traces of xylose.

General Growth Characteristics—MA-4830

Good growth on yeast extract-malt extract (YME), glucose asparaginase (GAs), inorganic salts-starch (ISS), oatmeal (Oat), sigma water (SW), Czapek (CZ), Peptone Iron agars. Culture also grows well in yeast extract dextrose (YED) broth. MA-6825—Good growth on YME, GAs, ISS, Oat, SW, CZ, Peptone Iron agars. Culture also grows well in YED broth. Growth occurs at 27° and 37° C. for both strains.

Colony morphology—MA-4830—(On YME 21 d)

Substrate mycelium is medium olive brown (95 m. Ol Br) and leathery in texture. Colonies are opaque, raised and erose. Aerial mycelium is initially white, turning to light brown gray (63 1 br Gy). Spore mass is gray to black. MA-6825—Substrate mycelium is brown gray (64 br Gy) and leathery. Colonies are opaque, raised and erose. Spore mass is gray to black.

Micromorphology—MA-4830

Aerial mycelium (0.76 μm dia.) arises from a substrate mycelium and is branched and flexous. In mature cultures, the aerial mycelium commonly terminates in tightly coiled spirals. Aerial growth tends to coalesce into amorphous masses as the culture ages. MA-6825—Aerial mycelium (0.76 μm dia.) arises from a substrate mycelium and is branched and flexous. In mature cultures, the aerial mycelium commonly terminates in tightly coiled spirals. Aerial growth tends to coalesce into amorphous masses in older cultures.

Miscellaneous physiological reactions—MA-4830

No melanoid pigments produced in tryptone yeast extract broth, H$_2$S negative in peptone-iron agar. Culture produces a bright yellow, diffusible, non pH-dependent pigment on YME and ISS agar. Carbon α-D-lactose, β-D-lactose, D-maltose, D-mannitol, D-mannose, D-raffinose, L-rhamnose, sucrose, D-xylose; poor utilization of D-arabinose, L-arabinose; no utilization of xylose. MA-6825—No melanoid pigments produced in tryptone yeast extract broth, H$_2$S negative in peptone-iron agar. Starch hydrolyzed. Culture produces a bright yellow, diffusible, non pH-dependent pigment on YME and ISS agar. Carbon source utilization pattern is as follows: good utilization of L-arabinose, cellobiose, D-fructose, inositol, a-D-lactose, β-D-lactose, D-maltose, D-mannitol, D-mannose, D-raffinose, L-rhamnose, sucrose, D-xylose; poor utilization of D-arabinose; no utilization of xylose.

DNA Homology

These strains were found to exhibit 69–70% homology at Tm-25.

Diagnosis

The results of these studies show that strain MA-6825 exhibits a similarity in morphological and physiological characteristics to *Streptomyces hygroscopicus subsp. aureolacrimosus* (MA-4830). There are differences between these strains in the carbohydrate utilization patterns and some physiological differences were noted in the response of MA-6825 to certain substrates. Most notably, this culture was able to sporulate on D-fructose, D-maltose, D-mannose, D-raffinose, and α-D-glucose (control plate) whereas MA-4830 did not. DNA homology data indicates that the strains are related at the species level, but, distinct from one another. The relationship between these strains and *Streptomyces violaceusniger* (Str. hygroscopicus is a subjective synonym of Str violaceusniger, Bergey's Manual of Systematic Bacteriology, Vol 4, 1989) remains to be established. Both MA-6825 and MA-4830 exhibit marked differences in carbohydrate utilization patterns from most other validly named subspecies of Str. hygroscopicus. (Bergey's Manual of Determinative Bacteriology, 8th Ed., 1974) Only Str. hygroscopicus subsp ossamyceticus shown a high similarity to either MA-6825 or MA-4830 and can be defferentiated on the basis of the production of melanoid pigments.

| Carbohydrate utilization pattern of MA-4830 and MA-6825 at 21 days | | |
|---|---|---|
| Carbon source | Utilization by MA-4830 | Utilization by MA-6825 |
| D-arabinose | 2 | 2 |
| L-arabinose | 2 | 3 |
| cellobiose | 3 | 3 |
| D-fructose | 3 | 3 |
| inositol | 3 | 3 |
| α-D-lactose | 3 | 3 |
| β-D-lactose | 3 | 3 |
| D-maltose | 3 | 3 |
| D-mannitol | 3 | 3 |
| D-mannose | 3 | 3 |
| D-raffinose | 3 | 3 |
| L-rhamnose | 3 | 3 |
| sucrose | 3 | 3 |
| D-xylose | 3 | 3 |
| L-xylose | 0 | 0 |
| a-D-glucose (control) | 3 | 3 |

3 = good utilization, 2 = moderate utilization, 1 = poor utilization, 0 = no utilization.
Note
MA-6825 was found to sporulate on D-fructose, D-maltose, D-mannose, D-raffinose, and α-D-glucose, MA-4830 did not respond similarly.

| Cultural characteristics of MA-4830 and MA-4825 at 21 days | | | | |
|---|---|---|---|---|
| | Amount of Growth | | Aerial Mycelium and/or Spores | |
| Medium | MA-4830 | MA-6825 | MA-4830 | MA-6825 |
| Yeast Extract Malt Extract | good | good | Light brown gray (63 l. brGy) spiral sporophores | Brown gray (64 br. Gy) spiral sporophores |
| Glucose Asparagine | good | good | Brown gray (64 br.Gy) spiral sporophores | Brown gray (64 br.Gy) spiral sporophores |
| Inorganic Salts Starch | good | good | Light brown gray (63 l. brGy) spiral sporophores | Brown gray (64 br.Gy) spiral sporophores |
| Oatmeal | good | good | Light brown gray (63 l. byGy) spiral sporophores | Brown black (65 brBlack) |
| Tap Water | sparse | sparse | Medium gray (265 med Gy) spiral sporophores | Dark gray (267 d.Gy) |
| Czpek | good | good | White (263 White) spiral sporophores | Yellow gray (93 yGy) |
| Peptone Iron | good | good | | |

| | Soluble Pigments | | Rerverse Color | |
|---|---|---|---|---|
| Medium | MA-4830 | MA-6825 | MA-4830 | MA-6825 |
| Yeast Extract Malt Extract | bright yellow | bright yellow | Medium olive brown (95 m. OlBr) | Medium olive brown (95 m. OlBr) |
| Glucose Asparagine | bright yellow | bright yellow | Gray yellow (95 gy.Y) | dark gray yellow (91 d. gy.Y) |
| Inorganic Salts Starch | bright yellow | bright yellow | Medium yellow (87 m.Y) | Gray yellow (95 gy.Y) |
| Oatmeal | pale yellow | pale yellow | Gray green yellow (105 gy. | Olive gray (113 Ol.Gy) |
| Tap Water | none noted | none noted | medium gray (265 m.Gy) | Gray brown (62 gy.Br) |
| Czpek | none noted | | light gray yellow brown (79 l.gy.yBr) | Yellow gray (39 yGy) |
| Peptone Iron | melanin negative | melanin negative | | |

The morphological and cultural characteristics of MA-6864 and MA-6865 are substantially the same as those of MA-6825 and thus all the cultures have been characterized as *Streptomyces hygroscopicus*. The only difference are that culture MA-6865 has slightly less vigorous growth in Czapek of significant cultures but this difference is not sufficient to render MA-6865 a separate species from MA-6825 and MA-6864. In addition, somewhat better production of the compounds of this invention has been achieved with the MA-6865 culture then with the other cultures.

The above description is illustrative of strains of *Streptomyces hygroscopicus* MA-6825, MA-6864 and MA-6865 which can be employed in the production of the instant compounds. However, the present invention also embraces mutants of the above described microorganisms. For example, those mutants which are obtained by natural selection or those produced by mutating agents including ionizing radiation such as ultraviolet irradiation, or chemical mutagens such as nitrosoguanidine or the like treatments are also included within the ambit of this invention.

The instant compounds are produced during the aerobic fermentation of suitable aqueous nutrient media under conditions described hereinafter, with a producing strain of *Streptomyces hygroscopicus* MA-6825, MA-6864 and MA-6865. Aqueous media such as those used for the production of many antibiotic substances are suitable for use in this process for the production of this macrocyclic compound. Such nutrient media contain sources of carbon and nitrogen assimilable by the microorganism and generally low levels of inorganic salts. In addition, the fermentation media may contain small amounts of inorganic salts and traces of metals necessary for the growth of the microorganisms, and production of the desired compound. These are usually present in sufficient concentrations in the complex sources of carbon and nitrogen, which may be used as nutrient sources, but can, of course, be added separately to the medium if desired.

In general, carbohydrates such as sugars, for example dextrose, sucrose, maltose, lactose, dextran, cerelose, corn meal, oat flour, and the like, and starches are suitable sources of assimilable carbon in the nutrient media. The exact quantity of the carbon source which is utilized in the medium will depend, in part, upon the other ingredients in the medium, but it is usually found that an amount of carbohydrate between 0.5 and 5% by weight of the medium is satisfactory. These carbon sources can be used individually or several such carbon sources may be combined in the same medium.

Various nitrogen sources such as yeast hydrolysates, yeast autolysates, yeast cells, tomato paste, corn meal, oat flour, soybean meal, casein hydrolysates, yeast extracts, corn steep liquors, distillers solubles, cottonseed meal, meat extract and the like, are readily assimilable by *Streptomyces hygroscopicus* MA-6825, MA-6864 and MA-6865 in the production of the instant compounds. The various sources of nitrogen can be used alone or in combination in amounts ranging from 0.2 to 6% by weight of the medium.

Among the nutrient inorganic salts, which can be incorporated in the culture media are the customary salts capable of yielding sodium, potassium, magnesium ammonium, calcium, phosphate, sulfate, chloride, carbonate, and like ions. Also included are trace metals such as cobalt, manganese, and the like.

It should be noted that the media described hereinbelow and in the Examples are merely illustrative of the wide variety of media, which may be employed, and are not intended to be limitative.

The following are Examples of media suitable for growing strains of *Streptomyces hygroscopicus* MA-6825, MA-6864 and MA-6865.

Medium 1

| | | |
|---|---|---|
| Dextrose | | 1.0 g |
| Dextrin (Fisher) | | 10.0 g |
| Beef Extract (Difco) | | 3.0 g |
| Yeast Autolysate (Ardamine pH, Yeast Prod.) | | 5.0 g |
| NZ Amine Type E (Sheffield) | | 5.0 g |
| $MgSO_4 \cdot 7H_2O$ | | 0.05 g |
| Phosphate Buffer | | 2 ml |
| $CaCO_3$ | | 0.5 g |
| $dH_2O$ | | 1000 ml |
| pH | | 7.0–7.2 |
| Phosphate Buffer: | $KH_2PO_4$ | 91.0 g |
| | $Na_2HPO_4$ | 95.0 g |
| | $dH_2O$ | 1000 ml |
| | pH | 7.0 |

| Medium 2 | |
|---|---|
| Yeast Extract (Difco) | 4.0 g |
| Malt Extract (Difco) | 10.0 g |
| Dextrose | 4.0 g |
| $dH_2O$ | 1000 ml |
| Agar | 20 g |
| pH | 7.2 |

Medium 3
Basal

| | |
|---|---|
| Sucrose | 103 g |
| $K_2SO_4$ | 0.25 g |
| Glucose | 10 g |
| L-Asparagine | 1.8 g |
| Casamino Acids (Difco) | 0.1 g |
| $MgCl_2 \cdot 6H_2O$ | 10.12 g |
| Trace Element Mix A | 2 ml |
| $dH_2O$ | to 700 ml |
| Agar | 22.0 g |

Post-sterilization additions, per 700 ml Basal:
100 ml of $CaCl_2$ solution (29.5 g/1000 ml $dH_2O$)
100 ml of $KH_2PO_4$ solution (0.5 g/1000 ml $dH_2O$)
100 ml of Tes solution (0.3 g Tris HCl + 0.1 g EDTA +
0.14 g NaCl in 1000 ml $dH_2O$, adjust to pH 8.0)

| Trace Element Mix A Composition | |
|---|---|
| $Fe(SO_4)_3 \cdot 7H_2O$ | 250 mg |
| $MnCl_2 \cdot 4H_2O$ | 500 mg |
| $CuCl_2 \cdot 2H_2O$ | 25 mg |
| $CaCl_2 \cdot 2H_2O$ | 1000 mg |
| $H_3BO_3$ | 50 mg |
| $(NH_4)_6Mo_7O_{24} \cdot 4H_2O$ | 20 mg |
| $ZnSO_4 \cdot 7H_2O$ | 100 mg |
| $Co(NO_3)_2 \cdot 6H_2O$ | 20 mg |
| 0.1N HCl | 1000 ml |

| Medium 4 | |
|---|---|
| Dextrin (Fisher) | 40 g |
| Distillers Solubles (Grain Processing Corp.) | 7 g |
| Yeast Extract (Oxoid) | 5 g |
| $CoCl_2 \cdot 6H_2O$ | 50 mg |
| $dH_2O$ | 1000 ml |
| pH | 7.3 |

| Medium 5 | |
|---|---|
| Dextrose | 45 g |
| Peptonized Milk (Sheffield) | 24 g |
| Ardamine pH (Yeast Products, Inc.) | 2.5 g |
| Polyglycol 2000 (Dow) | 2.5 ml |
| $dH_2O$ | 1000 ml |
| pH | 7.0 |

| Medium 6 | |
|---|---|
| Dextrose | 2.0% |
| Yeast Extract (Difco) | 2.0 |
| Casamino Acids (Difco) | 2.0 |
| $KNO_3$ | 0.2 |
| $MgSO_4 \cdot 7H_2O$ | 0.05 |
| NaCl | 0.05 |
| $FeSO_4 \cdot 7H_2O$ | 0.0025 |
| $CaCl_2 \cdot 7H_2O$ | 0.002 |
| $ZnSO_4 \cdot 7H_2O$ | 0.001 |
| $MnSO_4 \cdot H_2O$ | 0.0005 |
| $dH_2O$ | 1000 ml |
| pH | 7.0 with NaOH |

Medium 7

| -continued | |
|---|---|
| Dextrose | 0.1% |
| Soluble Starch (Fisher) | 1.0 |
| Beef Extract (Difco) | 0.3 |
| Yeast Autolysate (Ardamine pH Yeast Products) | 0.5 |
| NZ Amine Type E (Sheffield) | 0.5 |
| MgSO$_4$.7H$_2$O | 0.005 |
| KH2PO$_4$ | 0.0182 |
| Na$_2$.HPO$_4$ | 0.0190 |
| CaCO$_3$* | 0.05 |
| dH$_2$O | 1000 ml |
| pH | 7.0–7.2 with NaOH |

*Added after pH adjustment

The fermentations employing *Streptomyces hygroscopicus* MA-6825, MA-6864 and MA-6865 can be conducted at temperatures ranging from about 20° C. to about 40° C. For optimum results, it is most convenient to conduct these fermentations at a temperature in the range of from about 24° C. to about 30+ C. Temperatures of about 27°–28° C. are most preferred. The pH of the nutrient medium suitable for producing the instant compounds can vary from about 5.0 to 8.5 with a preferred range of from about 6.0 to 7.5.

Small scale fermentations are conveniently carried out by placing suitable quantities of nutrient medium in a flask employing known sterile techniques, inoculating the flask with either spores or vegetative cellular growth of *Streptomyces hygroscopicus* MA-6825, MA-6864 or MA-6865, loosely stoppering the flask with cotton and permitting the fermentation to proceed in a constant room temperature of about 28° C. on a rotary shaker at from 95 to 300 rpm for about 2 to 10 days. For larger scale work, it is preferable to conduct the fermentation in suitable tanks provided with an agitator and a means of aerating the fermentation medium. The nutrient medium is made up in the tank and after sterilization is inoculated with a source of vegetative cellular growth of *Streptomyces hygroscopicus* MA-6825, MA-6864 or MA-6865. The fermentation is allowed to continue for from 1 to 8 days while agitating and/or aerating the nutrient medium at a temperature in the range of from about 24° to 37° C. The degree of aeration is dependent upon several factors such as the size of the fermentor, agitation speed, and the like. Generally the larger scale fermentations are agitated at about 95 to 500 RPM and about 50 to 500 liters per minute of air.

The novel compounds of this invention are found primarily in the mycelium on termination of the *Streptomyces hygroscopicus* MA-6825, MA-6864 and MA-6865 fermentations and may be removed and separated therefrom as described below.

The separation of the novel compounds from the whole fermentation broth and the recovery of said compounds is carried out by solvent extraction and application of chromatographic fractionations with various chromatographic techniques and solvent systems.

The instant compounds have slight solubility in water, but are soluble in organic solvents. This property may be conveniently employed to recover the compound from the fermentation broth. Thus, in one recovery method, the whole fermentation broth is combined with approximately an equal volume of an organic solvent. While any organic solvent may be employed, it is preferable to use a water immiscible solvent such as ethyl acetate, methylene chloride, chloroform, methyl ethyl ketone and the like. Generally several extractions are desirable to achieve maximum recovery. The solvent removes the instant compounds as well as other substances lacking the antiparasitic activity of the instant compounds. If the solvent is a water immiscible one, the layers are separated and the organic solvent is evaporated under reduced pressure. If the solvent is water miscible, it can be extracted with a water immiscible solvent to separate the entrained water. This solvent can then be concentrated under reduced pressure. The residue is placed onto a chromatography column containing preferably, silica gel. The column retains the desired products and some impurities, but lets many of the impurities, particularly the nonpolar impurities, pass through. The column is washed with a moderately polar organic solvent such as methylene chloride, chloroform or hexane to further remove impurities, and is then washed with a mixture of methylene chloride, chloroform or hexane and an organic solvent of which acetone, ethyl acetate, methanol, and ethanol and the like are preferred. The solvent is evaporated and the residue further chromatographed using column chromatography, thin layer chromatography, preparative layer chromatography, high pressure liquid chromatography and the like, with silica gel, aluminum oxide, dextran gels and the like, as the chromatographic medium, with various solvents and combinations of solvents as the eluent. Thin layer, high pressure, liquid and preparative layer chromatography may be employed to detect the presence of, and to isolate the instant compounds. The use of the foregoing techniques as well as others known to those skilled in the art, will afford purified compositions containing the instant compounds. The presence of the desired compounds is determined by analyzing the various chromatographic fractions for biological activity against selected parasites, or physicochemical characteristics. The structures of the instant compounds have been determined by detailed analysis of the various spectral characteristics of the compounds, in particular their nuclear magnetic resonance, mass, ultraviolet and infrared spectra.

Based on these experimental data, the instant compounds are believed to have the following structural formulae:

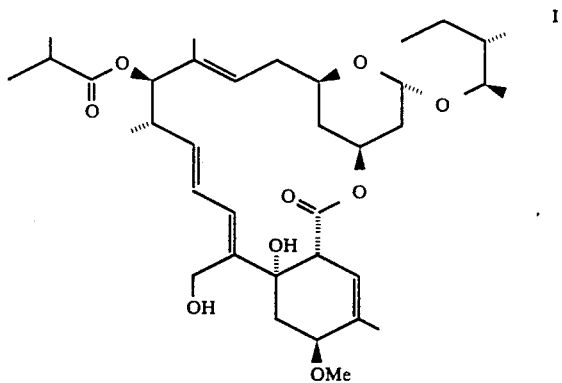

$^{13}$C NMR Data in CDCl$_3$ Solution: Chemical shifts for $^{13}$C spectra recorded in CDCl$_3$ solution are given in ppm relative to tetramethylsilane (TMS) at zero ppm using the solvent peak at 77.00 ppm as an internal standard: 11.35, 17.50, 17.87, 18.98, 19.01, 19.29, 19.34, 27.67, 34.36×2, 35.59, 36.48, 36.77, 37.25, 40.08, 40.96, 48.96, 56.75, 57.86, 67.02, 68.50, 71.41, 75.78, 76.80, 82.78, 97.54, 118.30, 125.44, 126.07, 129.30, 135.05, 138.56, 139.04, 141.01, 173.43, 176.14.

1H NMR data

MS: This compound has the molecular formula $C_{36}H_{54}O_9$ (calc 630.3768; found 630.3782) and forms a di-TMS derivative. Characteristic fragment ions in the EI spectra are observed at m/z 153/181 (defining C17-C25), 488 ([M-142], defining C1-C5 with a C5-O-methyl, 542 ([M-88] for loss of a C4 acid moiety) 265 ($C_{16}H_{25}O_3$, calc. 265.1804, found 265.1797; defining C13-C25 bearing oxygen at C13). The lack of an ion at m/z 151 coupled with the TMS count to indicate a β-type milbemycin.

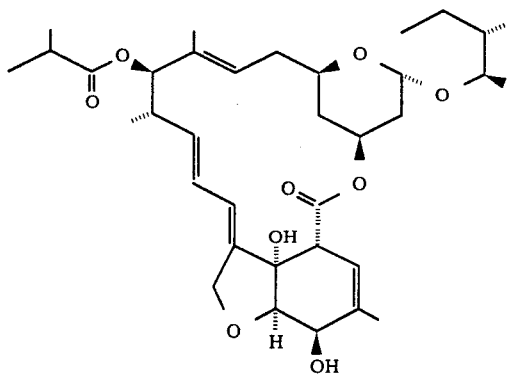

II

13C NMR Data in CDCl3 Solution:
Chemical shifts for 13C spectra recorded in CDCl3 solution are given in ppm relative to tetramethylsilane (TMS) at zero ppm using the solvent peak at 77.00 ppm as an internal standard: 10.91, 17.87, 18.60, 18.97, 19.00, 19.34, 19.95, 27.67, 34.33, 34.50, 35.59, 36.47, 36.73, 40.07, 41.04, 45.63, 67.00, 67.67, 68.49×2, 71.43, 79.23, 80.24, 83.26, 97.55, 118.11, 120.02, 124.55, 126.02, 135.49, 137.90, 140.96, 173.58, 176.15.

1H NMR data MS: This compound has the molecular formula $C_{35}H_{50}O_9$ (calc 614.3455; found 614.3460) and forms a di-TMS derivative. Characteristic fragment ions in the EI spectra are observed at m/z 153/181 (defining C17-C25), 486 ([M-128] defining C1-C5 with a C5-hydroxyl), 526 ([M-88] for loss of a C4 acid moiety), 265 (defining C13-C25 bearing oxygen at C13), and 151 (defining C6-C12 and an α-type milbemycin).

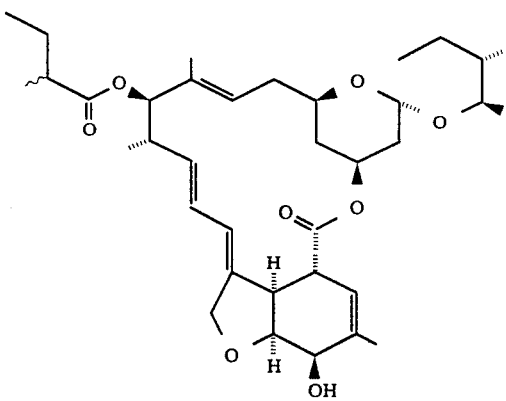

III

13C NMR Data in CDCl3 Solution:
Chemical shifts for 13C spectra recorded in CDCl3 solution are given in ppm relative to tetramethylsilane (TMS) at zero ppm using the solvent peak at 77.00 ppm as an internal standard. Carbons in the vicinity of the 2-methyl position of the ester side chain exhibit distinct chemical shifts for the two diastereomers whic integrate for approximately half the intensity of carbon resonances belonging to carbons which are remote from the ester side-chain and are enclosed in parenthesis and denoted as (×0.5): (10.93×0.5), (11.00×0.5), 17.87, (18.58×0.5), (18.62×0.5), 19.33, 19.95, 22.37, (25.83×0.5), (26.84×0.5), 27.67, 34.48, 35.59, 36.47, 36.73, (39.93×0.5), 39.98, 41.02, (41.38×0.5), 43.79, 45.63, 66.99, 67.67, 68.48×2, 71.42, 79.23, 80.24 (83.19×0.5), (83.29×0.5), 97.55, 118.11, 120.02, (124.54×0.5), (126.06×0.5), (126.15×0.5), (135.46×0.5), (135.51×0.5), (137.78×0.5), (137.86×0.5), 137.9, 140.95, 173.6×2.

1H NMR data

MS: This compound has the molecular formula $C_{36}H_{52}O_9$ (calc 628.3611; found 628.3645) and forms a di-TMS derivative. Characteristic fragment ions in the EI spectra observed at m/z 153/181 (defining C17-C25), 500 ([M-128] defining C1-C5 with a C5-hydroxyl), 526 ([M-102] for loss of a C5 acid moiety), 265 (defining C13-C25 bearing oxygen at C13), and 151 (defining C6-C12 and an α-type milbemycin).

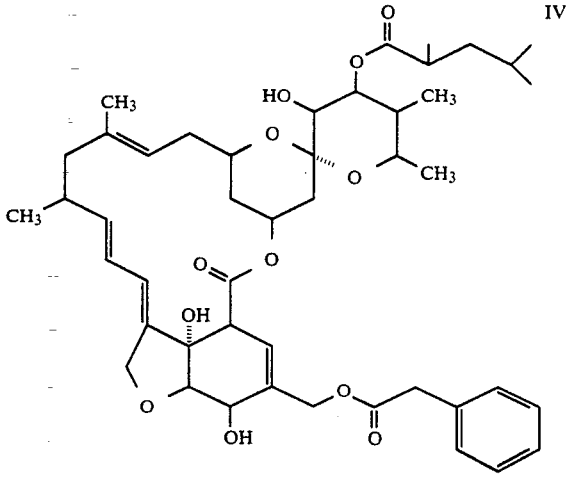

IV

13C NMR Data in CDCl3 Solution:
Chemical shifts for 13C spectra recorded in CDCl3 solution are given in ppm relative to tetrametylsilane (TMS) at zero ppm using the solvent peak at 77.00 ppm as an internal standard: 13.05, 15.56, 17.70, 18.84, 22.26, 22.41, 22.57, 25.86, 34.54, 35.97, 36.13, 36.16, 37.98, 41.30, 42.24, 42.92, 45.53, 48.51, 64.65, 64.72, 68.29, 68.51, 68.53, 69.38, 75.42, 75.48, 79.01, 80.34, 99.99, 120.32, 120.55, 121.88, 123.36, 127.11, 128.61×2, 129.29×2, 134.00 (weak), 136.36, 137.4 (weak), 139.18, 143.11, 171.30, 172.98, 177.91.

1H NMR data

MS: This compound has the molecular weight 806 by FAB-MS. EI exhibits a pseudo-molecular ion at m/z 670 which corresponds to [M-136] wherein the 136 moiety is phenylacetic acid as indicated by fragment ions at m/z 136 and 91 (as in compound V). HR-EI-MS affords $C_{38}H_{54}O_{10}$ (calc 670.372; found 670.382) which plus phenylacetic acid ($C_8H_8O_2$) yields $C_{46}H_{62}O_{12}$ for the molecular formula. Fragment ions indicate a milbemycin α5 analog wherein a phenyl acetic acid moiety is present at the C4 methyl position.

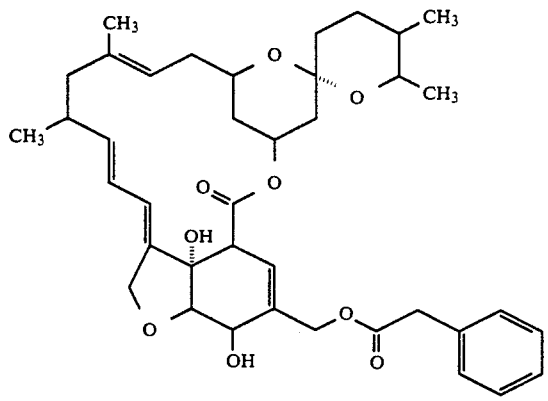

V

¹³C NMR Data in CDCl₃ Solution: Chemical shifts for ¹³C spectra recorded in CDCl₃ solution are given in ppm relative to tetramethylsilane (TMS) at zero ppm using the solvent peak at 77.00 ppm as an internal standard: 15.49, 17.87, 19.37, 22.28, 27.71, 34.68, 35.66, 35.97, 36.52, 36.61, 41.13, 41.18, 45.70, 48.53, 63.25, 67.48, 68.15, 68.60, 68.90, 71.34, 77.95, 80.72, 97.55, 120.55, 120.95, 122.78, 123.40, 127.23, 128.64×2, 129.29×2, 133.77, 136.78, 136.96, 138.98, 143.01, 171.30, 173.10.

¹H NMR data

MS: This compound has the molecular weight 662 by FAB and EI-MS. HR-EI-MS yielded the molecular formula $C_{39}H_{50}O_9$ (found 662.3466, calculated 662.3455). The pattern of characteristic fragment ions in the EI spectrum indicated an $α_1$ type milbemycin with a 135 amu ester moiety at the C4 CH₃ group. This moiety was assigned by NMR and MS as phenylacetic acid: characteristic phenylacetyl fragments at m/z 136, $C_8H_8O_2$ (Calc 136.0524; found 136.0522), and m/z 91 ($C_7H_7$, calc for 91.0548; found 91.0548).

The instant compounds are potent endo-and ecto-antiparasitic agents against parasites particularly helminths, ectoparasites, insects, and acarides, infecting man, animals and plants, thus having utility in human and animal health, agriculture and pest control in household and commercial areas.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats, fish, buffalo, camels, llamas, reindeer, laboratory animals, fur-bearing animals, zoo animals and exotic species and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Habronema, Druschia, Heterakis, Toxocara, Ascaridia, Oxyuris, Ancylostoma, Uncinaria, Toxascaris and Parascaris. Certain of these, such as Nematodirus, Cooperia, and Oesophagostomum attack primarily the intestinal tract while others, such as Haemonchus and Ostertagia, are more prevalent in the stomach while still others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The compounds of this invention have unexpectedly high activity against these parasites, and in addition are also active against Dirofilaria in dogs and cats, Nematospiroides, Syphacia, Aspiculuris in rodents, arthropod ectoparasites of animals and birds such as ticks, mites, lice, fleas, blowflies, in sheep Lucilia sp., biting insects and such migrating diperous larvae as Hypoderma sp. cattle, Gastrophilus in horses, and Cuterebra sp. in rodents and nuisance flies including blood feeding flies and filth flies.

The instant compounds are also useful against parasites which infect humans. The most common genera of parasites of the gastro-intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunuculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp., the housefly Musca domestica as well as fleas, house dust mites, termites and ants.

The compounds are also useful against insect pests of stored grains such as Tribolium sp., Tenebrio sp. and of agricultural plants such as aphids, (Acyrthiosiphon sp.); against migratory orthopterans such as locusts and immature stages of insects living on plant tissue. The compounds are useful as a nematocide for the control of soil nematodes and plant parasites such as Meloidogyne sp. which may be of importance in agriculture. The compounds are also highly useful in treating acerage infested with fire ant nests. The compounds are scattered above the infested area in low levels in bait formulations which are broght back to the nest. In addition to a direct-but-slow onset toxic effect on the fire ants, the compound has a long-term effect on the nest by sterilizing the queen which effectively destroys the nest.

The compounds of this invention may be administered in formulations wherein the active compound is intimately admixed with one or more inert ingredients and optionally indlucing one or more additional active ingredients. The compounds may be used in any composition known to those skilled in the art for administration to humans and animals, for application to plants and for premise and area application to control household pests in either a residential or commercial setting. For application to humans and animals to control internal and external parasites, oral formulations, in solid or liquid or parenteral liquid, implant or depot injection forms may be used. For topical application dip, spray, powder, dust, pour-on, spot-on, jetting fluid, shampoos, collar, tag or harness, may be used. For agricultural premise or area applications, liquid spray, powders, dust, or bait forms may be used. In addition "feed-through" forms may be used to control nuisance flies that feed or breed in animal waste. The compounds are formulated, such as by encapsulation, to lease a residue of active agent in the animal waste which controls filth flies or other arthropod pests.

These compounds may be administered orally in a unit dosage form such as a capsule, bolus or tablet, or as a liquid drench where used as an anthelmintic in mammals. The drench is normally a solution, suspen· or dispersion of the active ingredient usually in w:  ;o-gether with a suspending agent such as bentonite ...d a wetting agent or like excipient. Generally, the drenches also contain an antifoaming agent. Drench formulations generally contain from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or di-calcium phosphate.

Where it is desired to administer the instant compounds in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents, and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets or liquid which may then be added to the finished feed or optionally fed separately. Alternatively, feed based individual dosage forms may be used such as a chewable treat. Alternatively, the antiparasitic compounds of this invention may be administered to animals parenterally, for example, by intraruminal, intramuscular, intravascular, intratracheal, or subcutaneous injection in which the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol formal, propylene glycol, and aqueous parenteral formulations are also used. The active compound or compounds are dissolved or suspended in the parenteral formulation for administration; such formulations generally contain from 0.0005 to 5% by weight of the active compound.

Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites and other biting arthropods in domesticated animals and poultry. They are also effective in treatment of parasitic diseases that occur in other animals including humans. The optimum amount to be employed for best results will, of course, depend upon the particular compound employed, the species of animal to be treated and the type and severity of parasitic infection or infestation. Generally good results are obtained with our novel compounds by the oral administration of from about 0.001 to 10 mg per kg of animal body weight, such total dose being given at one time or in divided doses over a relatively short period of time such as 1-5 days. With the preferred compounds of the invention, excellent control of such parasites is obtained in animals by administering from about 0.025 to 0.5 mg per kg of body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active compounds are intimately dispersed throughout the carrier by methods such as grinding, stirring, milling or tumbling. Compositions containing from about 0.005 to 2.0% weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular compound employed, the compounds of this invention are usually fed at concentrations of between 0.00001 to 0.002% in the feed in order to achieve the desired anti-parasitic result.

In using the compounds of this invention, the individual compounds may be prepared and used in that form. Alternatively, mixtures of the individual compounds may be used, or other active compounds not related to the compounds of this invention.

The compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

The following examples are provided in order that this invention might be more fully understood; they are not to be constructed as limitative of the invention.

EXAMPLE 1

A frozen vial of spores of the culture MA 6865 (ATCC 55146) was inoculated into 50 ml of medium 1 (seed medium) in a 250 ml baffled erlenmeyer flask and incubated for three days at 28° C. with agitation on a rotary shaker at 220 rpm with a 5 cm throw.

Two ml of this seed was inoculated into 40 ml of medium 8 (growth medium) in each of 100, 250 ml baffled erlenmeyer flasks with agitation on a rotary shaker at 220 rpm with a 5 cm throw. Incubation was continued for 10 days.

| Medium 8 | |
| --- | --- |
| Figs | 30.0 g |
| Dextrin | 15.0 g |
| Primary yeast | 10.0 g |
| $CoCl_2.6H_2O$ | 10.0 mg |
| Beta cyclodextrin | 10.0 g |
| Distilled $H_2O$ | 1000 ml | pH 7.4 (adjust with NaOH)
ISOLATION

EXAMPLE 2

Whole broth (3.8 liters) was filtered and the filtrate discarded. The cell cake was extracted with two liters of acetone stirring for two hours, then filtered. The filtrate plus wash volume was 2.4 liters. The filtered acetone extract was concentrated to 450 ml. The concentrate was extracted with 2×450 ml of methylene chloride. An HPLC analysis of the extracts showed incomplete extraction and the aqueous layer was extracted with 600 ml of methyl ethyl ketone. HPLC analysis of the aqueous layer showed complete extraction. The methylene chloride and methyl ethyl ketone extracts were combined and concentrated to an oily residue.

EXAMPLE 3

The oily residue from Example 2 was taken up in 10 ml of 3:2 methylene chloride:methanol, to a total volume of 16 ml. The solution was chromato-graphed on 1.6 liters of LH-20 using methanol at a flow rate of 20 ml/min. collecting 20 ml fractions. Fractions 40 through 55 were combined on the basis of HPLC analysis and the combined fractions were concentrated to dryness. Residue 2.1 grams.

EXAMPLE 4

A one liter column of E. Merck silica-gel 60, 230–400 mesh, was prepared in 5:1 hexane:acetone. The 2.1 gram residue from Example 3 was taken up in 9:1 hexane:acetone, to a volume of 20 ml. The solution was chromatographed using 5:1 hexane:acetone at a flow rate of 20 ml/min. collecting 2×400 ml forecuts followed by one hundred and eight 20 ml fractions. The chromatography was continued based upon HPLC using 3:1 hexane:acetone at the same flowrate collecting fifty 20 ml fractions were combined as follows:

| Fractions | Labels |
| --- | --- |
| 5 thru 11 | A |
| 12 thru 15 | B |
| 16 thru 30 | C |
| 31 thru 49 | D |
| 50 thru 59 | E |
| 60 thru 75 | F |
| 76 thru 103 | G |
| 114 thru 129 | H |
| 130 thru 139 | J |

EXAMPLE 5

Two hundred ml of Fraction D from Example 4 was concentrated to dryness. The residue was taken up in 250 mcl of methanol and chromatographed on a DuPont Zorbax ODS 2.21×25 cm column a 60° C. using a solvent system of 87/13 methanol/water at a flow rate of 10 ml/min. The effluent stream was monitored at 243 nm using a Gilson model 116 U.V. detector, equipped with 0.05 mm path length cell, and a setting of 20 AUFS. The fraction with an Rt at 18.8 min. corresponding to the uv absorbance at 243 um was concentrated to dryness yielding 7 mg. of compound I.

EXAMPLE 6

Two hundred and fifty ml of fraction E from Example 4 was concentrated to dryness. The residue was taken up 250 mcl of methanol and chromatographed on a DuPont Zorbax ODS 2.21×25 cm column at 60° C. using a solvent system of 87/13 methanol/water at a flow rate of 10 ml/min. The effluent stream was monitored at 243 nm using a Gilson model 116 U.V. dector equipped with a 0.05 mm path length cell and a setting of 4 AUFS. The fraction with an Rt of 18.4 min corresponding to a uv absorbance at 245 nm was concentrated to dryness yielding g 2.2 mg. of compound II. The fraction with an Rt at 23.7 min., also with the same uv absorbance was concentrated to dryness yielding 1.6 mg of compound III.

EXAMPLE 7

Three hundred ml of Fraction H from Example 4 was concentrated to dryness. The residue was taken up in 250 mcl of methanol and chromatographed on a DuPont Zorbax ODS 2.21×25 cm column at 60° C. using a solvent system of 87/13 methanol/water at a flow rate of 10 ml/min. The effluent stream was monitored at 243 nm using a Gilson model 116 U.V. detector equipped with a 0.05 mm path length cell and a setting of 2 AUFS. The fraction with an Rt at 28.6 min. corresponding to a uv absorbance at 243 nm was concentrated to dryness yielding 1.8 mg. of compound IV. The fraction with a Rt at 38.2 min, also with the same uv absorbance was concentrated to dryness yielding 2.2 mg of compound V.

What is claimed is:

1. Compounds having the formulae

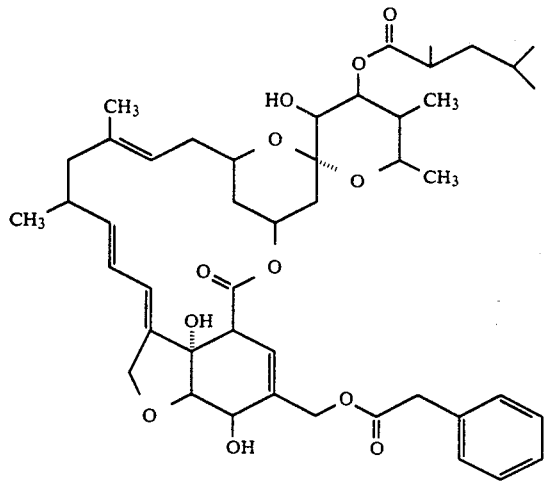

or

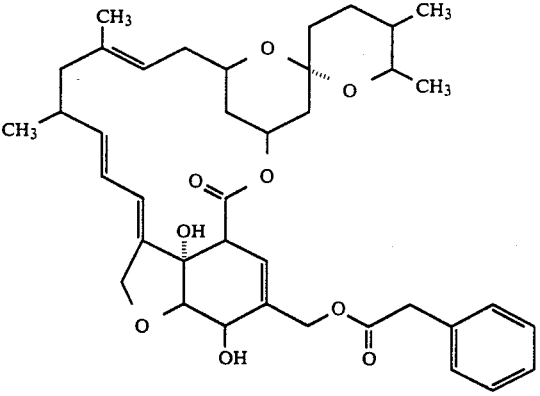

2. A compound of claim 1 which is Compound IV.
3. A compound of claim 1 which is Compound V.
4. A method for the treatment of parasitic infections of animals or parasitic infestations of plants or premises which comprises administering to such animal or plant or applying to such premise an effective amount of a compound of claim 1.
5. A composition effective for treating parasitic infections of animals or parasitic infestations of plants or premises which comprises a compound of claim 1 and an inert carrier.

* * * * *